United States Patent [19]

Fonger et al.

[11] Patent Number: 5,291,896
[45] Date of Patent: Mar. 8, 1994

[54] CARDIAC OUTPUT PROBE ASSEMBLY

[75] Inventors: James D. Fonger, Wayland, Mass.; David L. Swendson, Garden Grove, Calif.; Clifford E. Currier, Aliso Viejo, Calif.; David J. Evans, Irvine, Calif.; Donald E. Bobo, Jr., Orange, Calif.

[73] Assignee: Baxter International Inc., Deerfield, Ill.

[21] Appl. No.: 748,484

[22] Filed: Aug. 21, 1991

[51] Int. Cl.⁵ .............................. A61B 5/00; A61B 8/12
[52] U.S. Cl. .................................. 128/713; 128/662.06; 128/642; 604/264
[58] Field of Search ............... 128/642, 662.04–662.06, 128/419 P, 419 PT, 785–786; 604/43, 264

[56] References Cited

U.S. PATENT DOCUMENTS

| | | | |
|---|---|---|---|
| 3,087,486 | 4/1963 | Kilpatrick | 128/642 |
| 4,152,952 | 9/1978 | Thomas et al. | 128/785 |
| 4,294,258 | 10/1981 | Bernard | 128/642 X |
| 4,541,433 | 9/1985 | Baudino | 128/662.04 X |
| 4,585,013 | 4/1986 | Harris | 128/419 P X |
| 4,602,645 | 7/1986 | Barrington et al. | 128/419 P X |
| 4,771,788 | 9/1988 | Millar | 128/662.04 X |
| 4,865,037 | 9/1989 | Chin et al. | 128/786 X |
| 4,886,065 | 12/1989 | Collins, Jr. | 128/642 |
| 4,915,113 | 4/1990 | Holman | 128/662.04 X |
| 4,957,110 | 9/1990 | Vogel et al. | 128/642 |
| 5,046,503 | 9/1991 | Schneiderman | 128/662.06 X |
| 5,129,404 | 12/1990 | Spehr et al. | 128/785 |

Primary Examiner—Francis Jaworski
Attorney, Agent, or Firm—Bruce M. Canter

[57] ABSTRACT

A cardiac output probe assembly is disclosed wherein the assembly includes a chest tube which carries a cardiac output probe therein. The chest tube includes a main lumen for draining fluids from the thoracic cavity of the chest and a secondary lumen which carries leads attached to the probe. The probe is attached to the pulmonary artery or aorta vessel with detachable tines and/or sutures. The tines are uniquely configured to ensure that good contact between the probe and vessel is maintained. When cardiac output monitoring is complete, a pulling force is applied to the probe leads extending out through a proximal end of the tube. The pulling force detaches the tines and sutures, releasing the probe from connection with the vessel. Further withdrawal of the leads through the tube retracts the probe within the tube, where it is housed until the tube is removed from the thoracic cavity.

29 Claims, 4 Drawing Sheets

CARDIAC OUTPUT PROBE ASSEMBLY

FIELD OF THE INVENTION

The invention relates to cardiac output devices, and, in particular, to devices which measure and monitor cardiac output following open heart surgery.

BACKGROUND OF THE INVENTION

Cardiac probes are commonly used to measure and/or monitor cardiac output, blood flow, and stroke volume. Typically the probes include an ultrasonic transducer which is inserted into the heart via a catheter or is attached to the exterior of the heart. The transducer is coupled to an external circuit which applies a high frequency electrical signal that causes the transducer to transmit ultrasonic energy through a vessel in the heart. The energy reflected in the vessel is then received by the transducer and sent to the external circuitry for analysis and quantification.

These types of cardiac output probes are often attached outside the pulmonary artery immediately following open heart surgery to measure and monitor cardiac output. Since the probe is connected to external circuitry and instrumentation, the chest is typically left open during the monitoring procedure, thereby restricting the time period after completion of the surgery during which these measurements can be made.

SUMMARY OF THE INVENTION

The preferred embodiment of the present invention comprises a cardiac output probe assembly which may be used to measure and monitor cardiac output during the post-operative recovery period following open heart surgery. The assembly comprises an elongated flexible chest tube having a proximal end which is inserted into the thoracic cavity of a patient. The tube includes a main lumen for draining fluids from the thoracic cavity and a secondary lumen which carries leads attached to a cardiac output probe. The probe is fastened to the pulmonary artery or aorta vessel with detachable tines and/or sutures and connected to appropriate monitoring devices to measure and monitor cardiac output.

When the desired measurements have been obtained, the probe is removed by applying a pulling force to the probe leads which releases the tines from connection with the vessel. The leads are further withdrawn from the tube to retract the probe within the chest tube where it housed until the chest tube is removed from the thoracic cavity.

The distal end of the tube includes a mouth portion and a semicircular shield portion. The main lumen terminates at the mouth portion and the secondary lumen terminates closely adjacent to the mouth portion such that the withdrawal of the probe is not impeded by the distal end of the tube. The distal end may also be generally circular wherein the termination point of the secondary lumen is displaced to enable the probe to be housed within the main lumen when fully retracted into the tube.

A multi-lumen tube accommodates several cardiac output devices and consolidates access to the thoracic cavity. The tube comprises a main lumen for draining fluids from the thoracic cavity and a plurality of secondary lumens which carry the leads for the cardiac output devices.

In accordance with a broader aspect of the present invention a medical device comprises a temporary implant comprising an attachment portion which detachably fastens the implant to tissue within a living body. A line is connected to the implant wherein the attachment portion is configured to cause release of the implant in response to a force on the line. The device further comprises a tube having a generally smooth outer surface to permit the tube to be withdrawn from tissue of the living body by pulling thereon. The tube is sized to permit the line to pass therethrough and has a mouth portion which receives the implant. The tube may comprise a wound drain and may have drain holes proximal to one end thereof. The implant may comprise a sensor, and the sensor may comprise a transducer which produces electrical signals. The line may comprise a wire for carrying electrical signals. The tube may have two lumens, one of which is substantially larger than the other, and the line may be disposed in the smaller of the two lumens. The smaller of the two lumens may terminate at a location spaced from the mouth portion.

The mouth portion may be sized to permit the implant to fit therein. The mouth portion may be formed by a shield portion of substantially semicircular cross section disposed on one side of the tube. The tube may comprise two lumens, one being substantially smaller than the other, the smaller of the two lumens being disposed on the same side of the tube as the shield portion. The tube may be flexible. The smaller of the lumens may have a slit therein extending from a proximal end of the tube through only a selected portion of the tube to permit the line to be removed from the lumen so that the tube can be cut to proper size without cutting the line. The implant may additionally comprise a body portion and that attachment portion may comprise at least one tine attached to the body portion. A distal end portion of the tine is spaced from a surface of said body portion to permit the distal end to be inserted into tissue such that the tissue is between the tine and the surface of the body portion. The tine may extend in a direction generally parallel to the surface of the body portion, wherein the tine is resilient so as to forcibly bias the tissue between the tine and the surface of the body portion against the surface of the body portion. The tine may have a proximal end portion which is attached to the body portion and which extends outwardly from the surface of the body portion. The tine may have a curved intermediate portion between the proximal end portion and the distal end portion. The transducing head may also include an eyelet or notch to provide suture tie areas for suturing the probe to the tissue with dissolving sutures.

A method of removing a temporary implant detachably attached to tissue within a living body comprises applying force to a line which is connected to the implant, utilizing the force to detach the implant from the tissue, and utilizing the force to draw the implant to a mouth portion of a tube disposed with the living body, and withdrawing the tube from the living body. The step of withdrawing may comprise retaining the implant at the mouth of the tube during the withdrawing. The mouth portion may open laterally to one side of the tube, and the method may additionally comprise guiding the line along a path disposed on the opposite side of the tube. The step of guiding the line may comprise passing the line through a lumen having a distal end spaced from the mouth portion. The method may additionally comprise the step of draining bodily fluids through the tube.

The present invention also provides a method of performing a surgical procedure so that an attached implant may be readily removed without further surgery comprising attaching a temporary implant to tissue within a living body and placing a tube in the living body such that a distal end of the tube is in general proximity to the implant, a proximal end of the tube extend out of the living body, a line attached to the implant passes through a lumen of the tube, and a portion of the line and a portion of the tube are accessible from outside the living body.

DETAILED DESCRIPTION OF THE INVENTION

Figure 1:
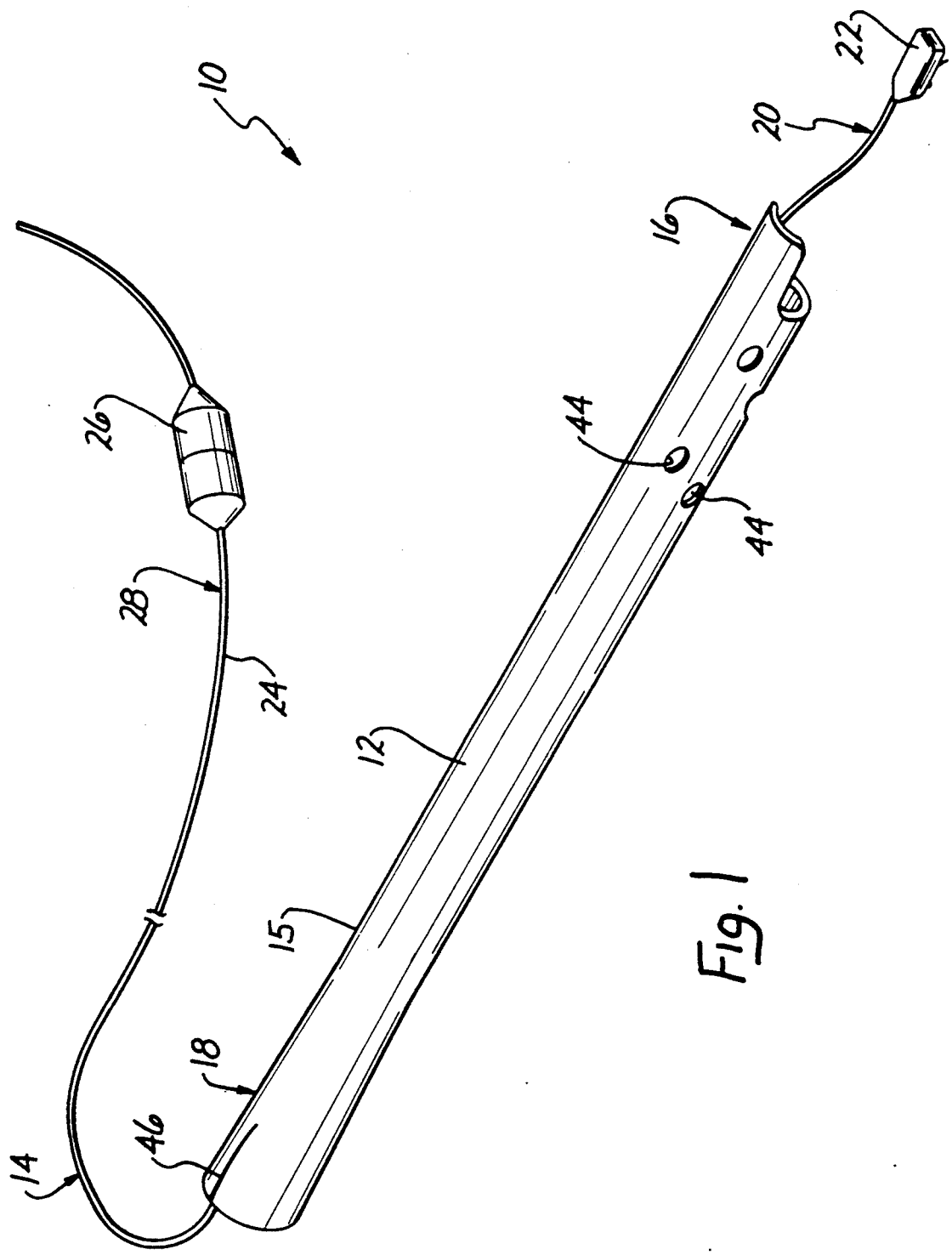
FIG. 1 is a perspective view of a cardiac output probe assembly in accordance with the present invention.

A cardiac output probe assembly 10 in accordance with the present invention is illustrated in FIG. 1. The assembly 10 comprises an elongated drainage tube 12 which carries a cardiac output probe 14 therein. The tube 12 has a generally smooth outer surface 15 and a preferred outside diameter in the range of 28-40 French. The tube 12 is preferably formed of a flexible biocompatible plastic such as PVC and includes a distal end 16 which is adapted for placement within the thoracic cavity of a living body and a proximal end 18 which extends for connection to a suitable drainage collection device (not shown). The probe 14 includes a distal end 20 having an implant such as a transducing head 22 which extends from the distal end 16 of the tube 12. The transducing head 22 is connected to electrical leads or wires enclosed in a line or cable 24 which extends through the tube 12 for connection to external circuitry and instrumentation (not shown) via an electrical connector 26 positioned at a proximal end 28 of the probe 14.

Figure 2:
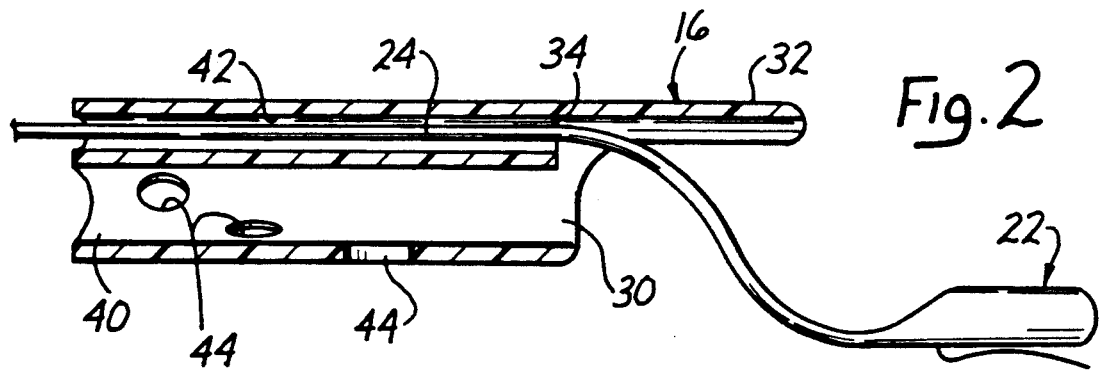
FIG. 2 is a partial cut-away view of the distal end of the tube.

Referring to FIG. 2, the distal end 16 of the tube 12 comprises a mouth portion 30 and a shield portion 32. The shield portion 32 has a substantially semicircular cross section and projects horizontally outwardly approximately 1 cm beyond the mouth portion 30 on one side 34 of the tube 12 to form a hood or shelf. The tube 12 contains a main drainage lumen 40 and a smaller secondary lumen 42 in which the probe leads 24 are carried. Preferably, the main lumen 40 has an inside diameter of approximately 20 French, while the secondary lumen 42 preferably has an inside diameter of approximately 10 French. The main lumen 40 extends through the length of the tube 12 and terminates at the mouth portion 30 while the secondary lumen 42 is disposed on the same side 34 of the tube 12 as the shield portion 32 and terminates slightly before the mouth portion 30 of the tube. The distal end 16 of the tube 12 further includes a plurality of apertures or drain holes 44 formed in the outer surface 15 of the tube in fluid communication with the main lumen 40. The proximal end 18 of the tube 12 includes an elongated slit 46 which extends through a selected portion preferably 7 cm in length along the outside wall 15 adjacent the secondary lumen 42.

Figure 3:
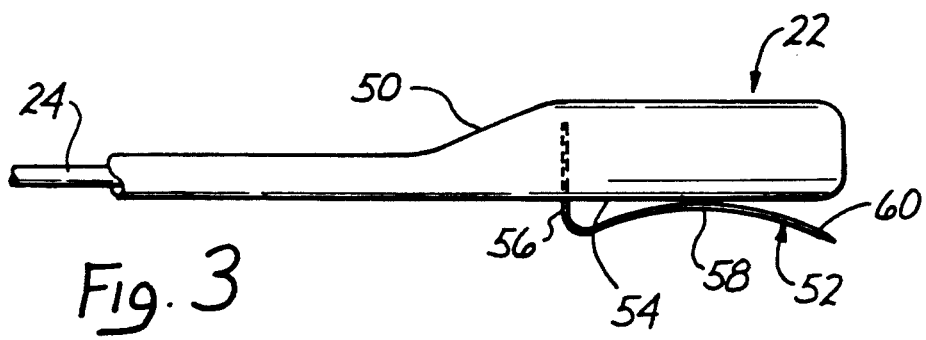
FIG. 3 is an enlarged view of the transducing head of the probe.

As illustrated in FIG. 3, the transducing head 22 comprises a generally rectangular housing or body portion 50 which encloses at least one sensor or transducer. The body portion 50 preferably comprises a silicone or urethane injection molded body having an attachment portion formed by a pair of resilient prongs or tines 52 embedded in a surface 54 thereof. Each tine 52 comprises a proximal end portion 56 which extends substantially perpendicular to the surface 54 of the body portion 50 of the transducing head 22 for attachment thereto. The tines further 52 include an intermediate portion 58 having a generally concave curvature and a similarly curved distal end portion 60 which extends to detachably fasten the transducing head 22 to body tissue or vessels.

The cardiac output probe assembly 10 of the present invention is advantageously implemented to measure and/or monitor cardiac output following open heart surgery. After completion of the surgery, the chest tube 12 is inserted beneath the rib cage and positioned in the thoracic cavity in a conventional manner, remaining in place during the post-operative recovery period. Adjustments to the length of the chest tube 12 can be made by cutting the proximal end 18 of the tube extending from the thoracic cavity. The slit 46 along the outer wall 15 of the tube 18 advantageously permits removal of the probe cable 24 from the tube 12 during this cutting process. Before cutting the proximal end 18 of the tube 12, the outer wall 15 of the tube is separated along the slit 46 and the portion of the probe cable 24 therein is temporarily removed. The proximal end 18 of the tube 12 is then cut to achieve the desired length and the probe cable 24 is reinserted through the slit 46 and repositioned within the secondary lumen 42. The drain holes 44 in the wall 15 of t he tube 12 enable blood and thoracic fluid which accumulate in the thoracic cavity during this recovery period to enter the main lumen 40 and drain out of the body through the chest tube 12, such that the chest tube functions as a wound drain.

Figure 4:
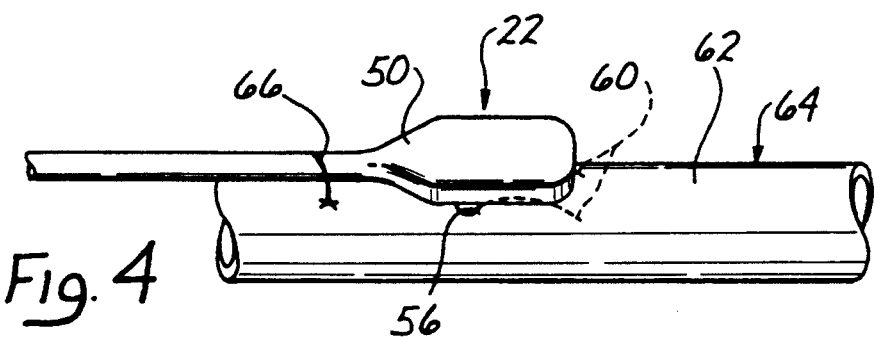
FIG. 4 illustrates the probe attached to a vessel.

The probe 14 is temporarily implanted in the exterior surface 62 of a pulmonary artery or aorta vessel 64 as illustrated in FIG. 4 by piercing the adventia of the vessel 64 with the distal portion 60 of the tines 52 and advancing the transducing head 22 until the intermediate portions 58 of the tines 52 are secured in the vessel 64. The transducing head 22 may be additionally secured with a suture 66 positioned adjacent the connection of the cable 24 to the body portion 50 of the head 22. When secured to the vessel 64 in this manner, the intermediate portions 58 of the tines 52 lie substantially parallel to the surface 54 of the transducing head 22 with the vessel 64 between the tines 52 and the surface 54, thereby restricting movement of the transducing head 22 relative to the vessel 64 to ensure that good contact between the vessel 64 and transducers 22 is maintained. The curvature and resiliency of the tines 52 further act to ensure that maximum contact pressure is maintained between the transducers and the vessel by forcibly biasing tissue at the periphery of the vessel 64 between the tines 52 and the surface 54 of the transducing head 22.

As described above, the probe leads 24 are carried within the secondary lumen 42 of the chest tube 12 and extend through the secondary lumen 42 outside the body for connection to external circuitry and instrumentation. Once the transducing head 22 has been attached to the vessel 64 in the manner described above, cardiac output measurements can be made by applying electrical signals to the transducing head 22 via the leads 24 carried within the chest tube 12. In response to the signals received from the external circuitry, the transducers output ultrasonic signals which are transmitted through the body portion 50 of the implant 22 to the vessel 64. Reflected signals are received by the transducers and transmitted back to the external circuitry and instrumentation where they are analyzed using well-known techniques to obtain cardiac output and/or flow data.

Figure 5:
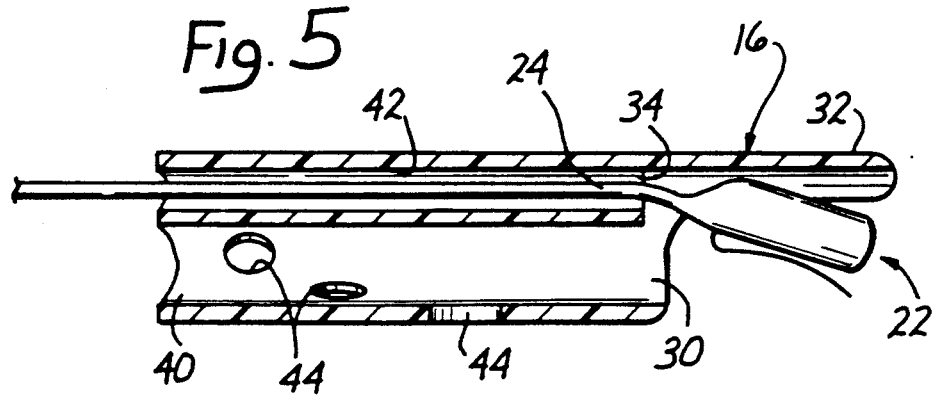
FIG. 5 shows the probe retracted within the tube.

With the present invention, the chest may be surgically closed following open heart surgery with the probe 14 affixed to the vessel 64 to measure and monitor cardiac output during the post-operative recovery period. Referring again to FIG. 1, when the desired cardiac output measurements have been obtained, such that the probe 14 is no longer needed, the probe 14 is removed from the body through the chest tube 12. To remove the probe 14, a pulling force is applied to the cable 24 which extends through the proximal end 18 of the chest tube 12 outside the body. The applied force acts to free the tines 52 and thereby suture(s) 66 attaching the probe 14 to the adventia and releases the transducing head 22 from connection with the vessel 64. The mouth portion 30 of the distal end 16 of the tube 12 receives the transducing head 22 as the cable 24 is withdrawn through the secondary lumen 42 and facilitates side entry of the transducing head 22 during this withdrawal process. The secondary lumen 42 which carries the probe leads 24 is advantageously configured to terminate sufficiently close to the mouth portion 30 of the tube such that the probe 14 is not retracted at an angle steep enough to cause the transducing head 22 to snag or catch on the mouth portion 30 of the tube 12 in response to the pulling force. Further retraction of the cable 24 draws the transducing head 22 beneath the shield portion 32 of the distal end 16 of the tube 12, as shown in FIG. 5, where it may be safely housed and retained until the chest tube 12 is removed from the body. Upon completion of the recovery period, the chest tube 12 and probe 14 housed therein are removed from the body by applying a pulling force on the tube 12.

Figure 6:
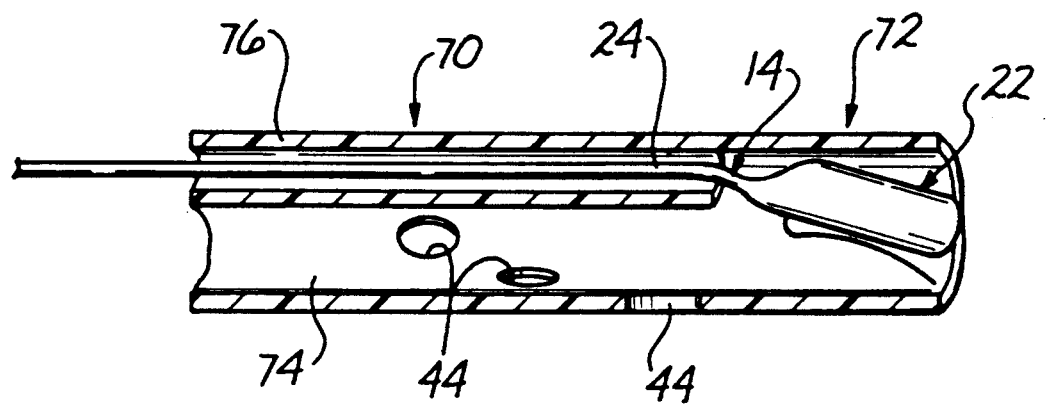
FIG. 6 is a partial cut-away view of a tube having a generally cylindrical distal end.

FIG. 6 illustrates another preferred embodiment of a chest tube 70 having a distal end 72 which is substantially circular. As in the embodiment described above, the tube 70 includes a main lumen 74 for draining fluids from the thoracic cavity and a secondary lumen 76 which carries the leads 24 connected to the transducing head 22 of the probe 14. The main lumen 74 terminates at the distal end 72 of the tube 70 while the termination point 78 of the secondary lumen 76 is displaced from the distal end 72. The amount of displacement is approximately equal to the length of the head 22, such that when the probe 14 is retracted int he chest tube 70 in the manner previously described, the transducing head 22 is completely enclosed by the chest tube 70, facilitating removal of the probe when the chest tube is withdrawn from the body.

Figure 7:
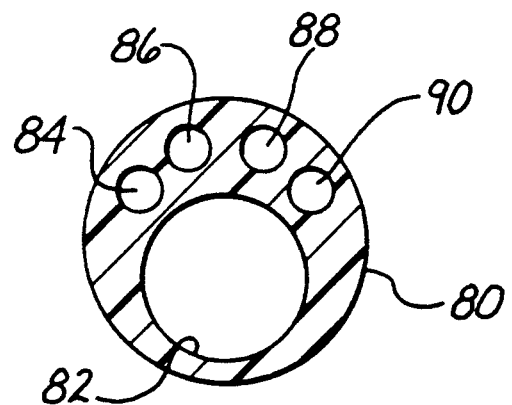
FIG. 7 is a cross-sectional view of a multi-lumen tube.

Another preferred embodiment of a chest tube 80 is illustrated in FIG. 7. The tube 80 comprises a plurality of lumens to accommodate a variety of cardiac output monitoring devices and consolidate access to the thoracic cavity. Consolidated access of this type is particularly advantageous in pediatric cardiac surgery where the chest area is not as large as in adult cardiac patients. The tube 80 comprises a first large lumen 82 through which blood and other fluids accumulating int he thoracic cavity may be drained. The tube 80 further comprises a plurality of smaller lumens through which other desired cardiac output devices may be carried. Preferably, four smaller lumens 84, 86, 88, 90 are provided which carry left atrial pressure sensor leads, right atrial pressure sensor leads, pacing leads, and flow probe leads, respectively, however, those skilled in the art will recognize that other numbers of secondary lumens and other types of monitoring devices could also be used.

A distal end of the chest tube is conventionally inserted into the thoracic cavity while a proximal end of the chest tube extends out of the body for connection to a suitable drainage device. The probe may be advanced through the fourth smaller lumen 90 and detachably fastened to the pulmonary artery or aorta vessel of the heart as described above. Pacing leads carried in the third smaller lumen 88 are advanced and then detachably attached to the epicardium to provide electric current to the heart in accordance with well-known pacing techniques. The left and right atrial pressure lines include fiber optic or solid state pressure transducers which are advanced through the lumens 84, 86 and detachably attached to the left and right atrium, respectively, to measure pressure in the left and right atrium in a well-known manner.

Upon completion of one or more of the desired cardiac monitoring functions, a force is applied to the leads of a selected device extending through the proximal end of the chest tube 80. The force acts to detach the selected device from the vessel or tissue. Further withdrawal of the selected leads through the respective lumen 84, 86, 88, 90 retracts the device within the tube.

The distal end of the tube 80 may comprise a mouth portion and a semicircular shield portion identical to those illustrated in FIG. 5, wherein the probe is received by the mouth portion and housed beneath the shield portion. The main lumen 82 terminals at the mouth portion and the secondary lumens 84, 86, 88 carrying the pressure sensing and pacing leads terminate closely adjacent the main lumen 82. The termination point of the secondary lumen 90 carrying the probe leads is again advantageously selected such that probe is not retracted at an angle steep enough to impede withdrawal of the transducing head within the tube 80. The pressure sensing and pacing devices are sufficiently small size to be withdrawn and housed within their respective lumens 84, 86, 88. Alternatively, the distal end of the tube 80 may be substantially circular as shown in FIG. 6, wherein the main lumen 82 terminates at the mouth and the lumen 90 carrying the probe leads terminates approximately 2 cm before the main lumen 82 such that the probe is housed inside the main lumen 82 at the distal end of the tube 80 when retracted. The remaining secondary lumens 84, 86, 88 terminate adjacent the main lumen 82 and the associated devices are housed directly within their respective lumens 84, 86, 88.

After the process of detaching the monitoring devices has been completed, the chest tube 80 is removed from the thoracic cavity in a conventional manner, and the devices are carried with the tube during such removal. Thus, it can be seen that the multi-lumen chest tube 80 and cardiac output assembly requires only one point of entry into the body, greatly consolidating access to the thoracic cavity.

Figure 8:
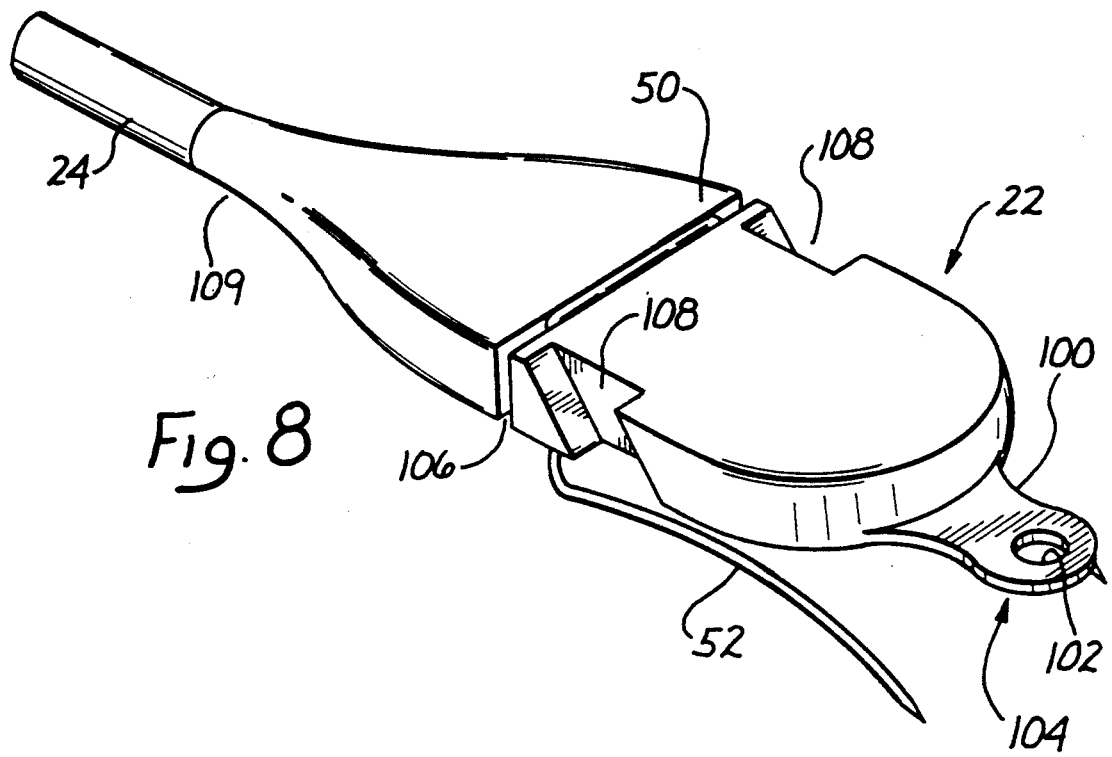
FIG. 8 illustrates another embodiment of a transducing head having a suture tie portion comprising an eyelet.

In a further aspect of the invention, the transducing head 22 may include a nose portion 100 having an aperture 102 therein forming an eyelet 104, as shown in FIG. 8. The probe 14 may be temporarily attached to the exterior surface of a blood vessel by threading a suture through the eye of the eyelet portion 104 of the head 22 and tying the suture around the vessel. The suture may be used as an alternative to, or in addition to, the tines 52. The tines 52 may be embedded in the body portion 50 of the transducing head 22, as previously illustrated, or mounted within a groove 106 formed in the head 22, as shown in FIG. 8. If desired, an additional suture may be tied around a neck portion 109 of the head adjacent the connection of the probe cable 24 to the body portion 50 of the head 22 to further secure the probe to the artery or vessel. The sutures are preferably made of a material which is gradually dissolved by the patient's body. The transducing head 22 may further include a pair of angled channels or notches 108 formed on the sides of the body portion 50. The notches 108 are sized and configured to receive the jaws of a pair of tweezers which may be used to grasp the transducing head 22 and secure the tines 52 in the vessel. The probe 14 may be retracted into a chest tube 12, 70, 80, as described above after the sutures have dissolved.

Figure 9:
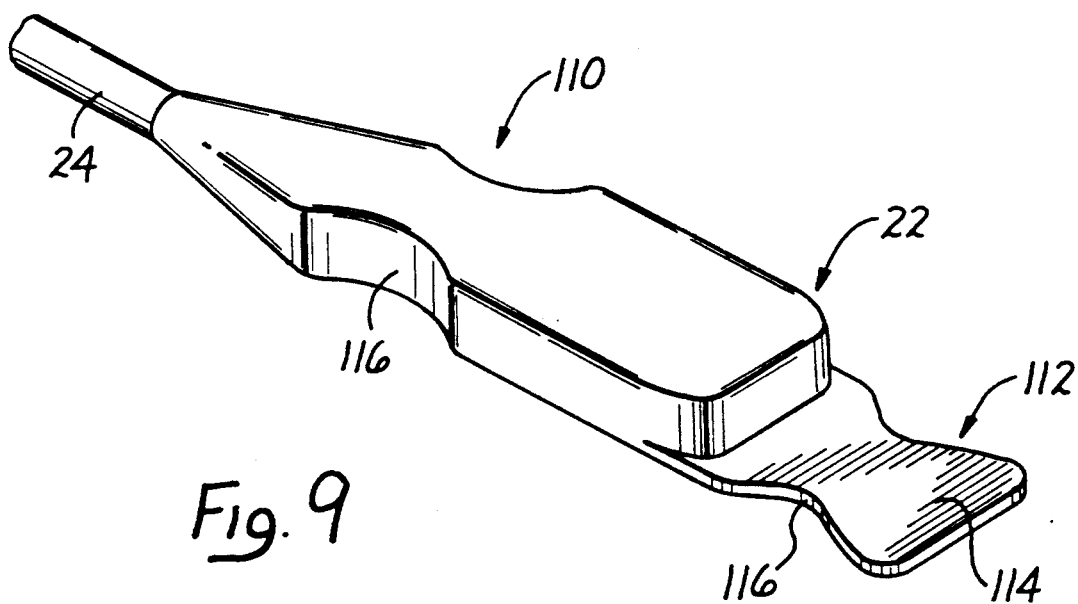
FIG. 9 illustrates a further embodiment of a transducing head having suture tie portions comprising notches.

In yet another aspect of the invention, shown in FIG. 9, the transducing head 22 of the probe 14 may include a first suture tie area 110 located adjacent the attachment of the probe cable 24 to the transducing head 22. A second suture tie area 112 is formed by a projecting nose portion 114 disposed at the distal tip of the transducing head 22. Each suture tie area 110, 112 has a generally "hourglass" shape including a notched or narrowed region 116. The probe 14 may be temporarily attached to the vessel with dissolving sutures placed across the notched regions 116 of the suture tie areas 110, 112 of the transducing head 22. Again, after the sutures have dissolved, the probe 14 may be retracted into a chest tube 12, 70, 80, in the manner previously described.

The invention may be embodied in other specific forms without departing from its spirit or essential characteristics. The described embodiments are to be considered in all respects only as illustrative and not restrictive. The scope of the invention is, therefore, indicated by the appended claims rather than the foregoing description. All changes which come within the meaning of the claims are to be embraced within their scope.

What is claimed is:

1. A medical device for use on extravascular tissue within a living body, comprising:
   a temporarily implantable cardiac output probe comprising an attachment portion which is adapted to detachably fasten said implantable probe to the extravascular tissue;
   a line, connected to said implantable probe, said attachment portion being configured to cause release of said implantable probe in response to a force on said line; and
   a chest tube having a generally smooth outer surface to permit said chest tube to be inserted into and enclosed within the thoracic cavity of the living body and to be withdrawn from the living body by pulling thereon, said tube sized to permit said line to pass therethrough, and having a mouth portion which receives said implantable probe prior to withdrawal of said chest tube from the thoracic cavity.

2. The device of claim 1, wherein said chest tube comprises a wound drain.

3. The device of claim 2, wherein said chest tube has drain holes proximal to one end thereof.

4. The device of claim 1, wherein said implantable probe comprises a transducer which produces electrical signals.

5. The device of claim 1, where said line comprises a wire for carrying electrical signals.

6. The device of claim 1, wherein said tube has two lumens, one of which is substantially larger than the other.

7. The device of claim 6, wherein said line is disposed in the smaller of said two lumens.

8. The device of claim 7, wherein the smaller of said lumens has a slit therein extending from a proximal end of said tube through only a selected portion of said chest tube to permit said line to be removed from said lumen so that said tube can be cut to proper size without cutting said line.

9. The device of claim 6, wherein the smaller of the two lumens terminates at a location spaced from said mouth portion.

10. The device of claim 1, wherein said mouth portion is sized to permit said implant to fit therein.

11. The device of claim 10, wherein said mouth portion is formed by a shield portion of substantially semi-circular cross section, said shield portion being disposed on one side of said tube.

12. The device of claim 11, wherein said tube comprises two lumens, one being substantially smaller than the other, the smaller of the two lumens being disposed on the same side of said tube as said shield portion.

13. The device of claim 1, wherein said chest tube is flexible.

14. The device of claim 1, wherein said implantable probe additionally comprises a body portion, and wherein said attachment portion comprises at least one tine, attached to said body portion.

15. The device of claim 14, wherein a distal end portion of said tine is spaced from a surface of said body portion to permit said distal end to be inserted into tissue, such that tissue is between the tine and the surface of said body portion.

16. The device of claim 15, wherein said tine extends in a direction generally parallel to said surface of said body portion, and wherein said tine is resilient so as to forcibly bias the tissue between said tine and said surface of said body portion against said surface of said body portion.

17. The device of claim 16, wherein said tine has a proximal end portion which is attached to said body portion and which extends outwardly from said surface of said body portion.

18. The device of claim 17, wherein said tine has a curved intermediate portion between said proximal end portion and said distal end portion.

19. The device of claim 1, wherein said attachment portion comprises a suture tie portion configured to receive a suture for attaching said implantable probe to the extravascular tissue.

20. The device of claim 1, wherein said attachment portion comprises a notched region across which at least one suture is placed to attach said implantable probe to the extravascular tissue.

21. A method of removing a temporarily implantable cardiac output probe, detachably attached to tissue within a living body, said method comprising:
  applying force to a line which is connected to said implantable probe;
  utilizing said force to detach said implantable probe from the tissue;
  utilizing said force to draw said implantable probe to a mouth portion of a chest tube enclosed within the thoracic cavity of the living body; and
  withdrawing said chest tube from the living body.

22. The method of claim 21, wherein the step of withdrawing comprises retaining the implantable probe at the mouth of the chest tube during the withdrawing.

23. The method of claim 22, wherein the mouth portion opens laterally to one side of the chest tube, said method additionally comprising guiding said line along a path disposed on the opposite side of said chest tube.

24. The method of claim 23, wherein the step of guiding said line comprises passing said line through a lumen having a distal end spaced from said mouth portion.

25. The method of claim 21, additionally comprising the step of draining bodily fluids through said chest tube.

26. A method of performing a surgical procedure so that an attached temporarily implantable cardiac output probe may be readily removed without further surgery, said method comprising:
  attaching a temporarily implantable cardiac output probe to tissue within a living body; and
  placing a chest tube in the living body such that (i) a distal end of said chest tube is in general proximity to said implantable probe, (ii) a proximal end of said chest tube extends out of the living body, (iii) a line attached to said implantable probe passes through a lumen of said chest tube, and (iv) a portion of said line and a portion of said chest tube are accessible from outside the living body.

27. A method of surgically attaching a temporarily implantable cardiac output probe and safely removing the implantable probe with further surgery, said method comprising:
  attaching a temporarily implantable cardiac output probe to tissue within a living body;
  placing a chest tube having a receptacle at its distal end in the living body such that the distal end of said chest tube is in general proximity to said implantable probe and a proximal end of said chest tube extends out of the living body;
  attaching a line to said implantable probe and passing said line through a lumen of said chest tube so that a portion of said line and a portion of said chest tube are accessible from outside the living body;
  applying force to said line to remove said implantable probe from the tissue and to place said implantable probe in the receptacle of said chest tube; and
  removing said chest tube and said implantable probe from the living body.

28. A medical device for use on extravascular tissue within a living body, comprising:
  a temporary implant comprising an attachment portion which is adapted to detachably attach fasten said probe to the extravascular tissue;
  a line, connected to said implant, said attachment portion being configured to cause release of said implant in response to a force on said line; and
  a chest tube having a generally smooth outer surface to permit said chest tube to be inserted into and enclosed within the thoracic cavity of the living body and to be withdrawn from the living body by pulling thereon, said tube sized to permit said line to pass therethrough, and having a mouth portion which is sized to permit said implant to fit therein and which receives said implant prior to withdrawal of said chest tube from the thoracic cavity.

29. The device of claim 28, wherein said mouth portion is formed by a shield portion of substantially semicircular cross section, said shield portion being disposed on one side of said tube.

* * * * *